US006274303B1

(12) United States Patent
Wowk et al.

(10) Patent No.: US 6,274,303 B1
(45) Date of Patent: Aug. 14, 2001

(54) METHOD FOR RAPID COOLING AND WARMING OF BIOLOGICAL MATERIALS

(76) Inventors: Brian G. Wowk, 35 Eastmount Drive, Winnepeg, Manitoba (CA), R2N3W7; Michael G. Federowicz, 4447 Tenth St., Riverside, CA (US) 92501; Sandra R. Russell, 553 Lomas Santa Fe Dr., Solana Beach, CA (US) 92075; Steven B. Harris, 2630 Stringham Ave., #A115, Salt Lake City, UT (US) 84109

( * ) Notice: Subject to any disclaimer, the term of this patent is extended or adjusted under 35 U.S.C. 154(b) by 0 days.

(21) Appl. No.: 09/310,167

(22) Filed: May 10, 1999

Related U.S. Application Data

(60) Division of application No. 08/966,187, filed on Nov. 7, 1997, now Pat. No. 5,952,168, which is a continuation-in-part of application No. 08/819,317, filed on Mar. 18, 1997, now abandoned.
(60) Provisional application No. 60/030,700, filed on Nov. 7, 1996.

(51) Int. Cl.$^7$ ...................................................... A01N 1/02
(52) U.S. Cl. ........................................................ 435/1.3
(58) Field of Search ............................... 435/1.1, 1.2, 1.3

(56) References Cited

U.S. PATENT DOCUMENTS

| | | |
|---|---|---|
| 4,471,629 | 9/1984 | Toledo-Pereyra . |
| 5,066,578 * | 11/1991 | Wikman-Coffelt ...................... 435/1 |
| 5,217,860 | 6/1993 | Fahy et al. . |
| 5,584,804 | 12/1996 | Klatz et al. . |
| 5,741,248 * | 4/1998 | Stern et al. ............................. 606/21 |

FOREIGN PATENT DOCUMENTS

| | | |
|---|---|---|
| 222 494 A1 | 5/1985 | (DE) . |
| 0 399 842 A2 | 11/1990 | (EP) . |

OTHER PUBLICATIONS

Lowe, Perfluorochemicals in Medicine. Chem. Ind. 1991, vol. 83, No. 3, pp. 86–90.
Beisang, et al., Damage assay of kidneys frozen by intraarterial perfusion with a fluorocarbon. Federation Proceedings, Sep.–Oct. 1970, vol. 29, No. 5, pp. 1782–1788.
Kolbeck, et al., Nonpolar density gradient ultracentrifugation in the direct determination of myocardial subcellular calcium. Journal of Molecular and Cellular Cardiology. 1985, vol. 17, No. 3, pp. 243–253.
Database CA on–line. An 114:80060, Heisei, 'Tissue culture efficiency improvement using prefluorocarbon'. JP 02211866 A@ BioChem Technology, Inc., Aug. 23, 1990, abstract.
Vorotilin, et al., Cryoprotective properties of ethylene glycol ethers during freezing of human erythrocytes. Kriobiologiya, 1987, vol. 3, pp. 31–4.
T. Suzuki, Fertilization and Development of Frozen–Thawed Germinal Vesicle Bovine Oocytes by a One–Step Dilution Method in Vitro. Cryobiology 33, pp. 515–524, 1996. Article No. 0055.
M. Takagi, et al., Postthaw Viability of the Inner Cell Mass of in Vitro–Matured/in Vitro–Fertilized Bovine Embryos Frozen in Various Cryoprotectants. Cryobiology 31, pp. 398–405, 1994.
M. Takagi, et al., Survival Rate of Frozen–Thawed Bovine IVF Embryos in Relation to Exposure Time Using Various Cryoprotectants. Cryobiology 30, pp. 306–312, 1993.
P. Schuff–Werner, et al., O–Methyl–rac–glycerol: A New Agent for the Cryopreservation of Mononuclear Cells. Cryobiology 25, pp. 487–494, 1988.
Grant, Roger, et al.; Grant & Hackh's Chemical Dictionary; Fifth Edition; pp. 266.
Wang, et al.; Cryobiology 28, 171–176 (1991); Freezing Preservation of Adult Mammalian Heart at High Subzero Temperatures.
Kaeser, et al.; Journal of Microscopy, vol. 154, Pt. 3, Jun. 1989, pp. 273–278; Freeze–substitution of plant tissues with a new medium containing dimethoxypropane.

* cited by examiner

*Primary Examiner*—Sandra E. Saucier
(74) *Attorney, Agent, or Firm*—Knobbe, Martens, Olson & Bear LLP

(57) ABSTRACT

A method of cooling and rewarming large organs and tissues at sub-zero temperatures is provided. The method includes perfusion of tissue with inert fluids that remain liquid at very low temperatures. The inert fluids can include fluorocarbons, silicones, or fluorosilicones. Glycol ethers are used as a novel class of cryoprotective agents for organ and tissue preservation. The glycol ethers have improved viscosity, penetration, and glass forming properties.

21 Claims, No Drawings

METHOD FOR RAPID COOLING AND WARMING OF BIOLOGICAL MATERIALS

RELATED APPLICATIONS

The present application is a divisional of U.S. application Ser. No. 08/966,187 filed Nov. 7, 1997, now U.S. Pat. No. 5,952,168 which is a continuation-in-part of U.S. application Ser. No. 08/819,317, filed Mar. 18, 1997, now abandoned which claims the benefit of priority under 35 U.S.C. §119(e) of U.S. Provisional Application No. 60/030,700, filed Nov. 7, 1996.

BACKGROUND OF THE INVENTION

The invention concerns a method for the temperature control of biological materials at sub-zero (below freezing) temperatures, particularly, a method for rapid internal cooling and rewarming of vascular organs and tissues with an inert fluid. This invention also relates to a class of new cryoprotective agents (CPA) used for organ cryopreservation and cryonics.

Biological processes can be greatly slowed at low temperatures, and even completely stopped at temperatures far below freezing. This principle is now successfully used to store at low temperatures (cryopreserve) and later recover a variety of living biological materials including cell cultures, blood, sperm, embryos, and skin. Chemical cryoprotective agents (CPAs) are added to the biological material prior to cooling to reduce ice formation and minimize the mechanical injury to the biological material caused by ice crystals formed during cooling.

One objective of organ cryopreservation is the long-term banking of transplantable organs at low temperatures until they are needed by recipients who are optimally matched for them. Technology to achieve this objective is the subject of ongoing research. Freezing and vitrification are two different approaches currently being pursued. For freezing, the organ to be cryopreserved is perfused with a sufficient concentration of cryoprotective agent so that ice formation is limited to non-lethal amounts during subsequent cooling. For vitrification, the organ is perfused with even higher concentrations of CPA so that ice formation is avoided completely on cooling (see U.S. Pat. No. 4,559,298, U.S. Pat. No. 5,217,860). In both cases, organs must be typically cooled to temperatures below $-100°$ C. for long-term stability.

Cryopreservation of organs or large organisms presents special problems as vascular tissues and the complex assemblages of cells which makes up the functional elements of parenchymatous organs (i.e. renal tubular architecture, neuronal interconnections and long processes) are more sensitive to injury by ice formation than small tissue samples or cell suspensions. Cryopreservation of vascularized tissue and solid organs with complex interdependent assemblages of cells requires replacement of a large fraction of cell and tissue water (usually by perfusion) with a high concentration of CPA to reduce ice formation to low levels, or to avoid ice formation completely by vitrification. This demanding application requires that CPAs be highly penetrating, non-toxic, and strongly inhibit ice formation. If vitrification is sought specifically, the CPA must also vitrify at low concentration, or be a "good glass former".

CPAs which have been explored for intracellular use in organ cryopreservation include dimethyl sulfoxide, alcohols, polyols (including ethylene glycol, propylene glycol, glycerol, butanediols), amides (including formamide, acetamide), and alkylamides (including methyl formamide, dimethyl formamide, diethylformamide). As yet, none of these agents or combination thereof have proven fully satisfactory for cryapreservation of large mammalian organs.

One objective of cryonics is to cryopreserve the entire human body or brain of a terminally-ill patient with sufficient fidelity that future medical technology might permit resuscitation and treatment. This objective is highly speculative at present. The long-term goal of cryonics research is the development of completely reversible means for maintaining humans in a state of arrested metabolism ("suspended animation"). The technologies and procedures used in cryonics are similar to those being developed for individual organ cryopreservation, except that they are applied to the whole body or brain.

For three decades, the CPA of choice in cryonics research has been glycerol. All the other agents tested proved to be excessively toxic to the central nervous system, causing edema and/or worsened ultrastructural preservation. However, the disadvantages of glycerol are numerous. It is viscous and does not penetrate mammalian cells readily at temperatures below $10°$ C., necessitating perfusion at relatively high temperatures, thereby exacerbating ischemic injury. It permeates poorly, causing massive dehydration and poor preservation of myelinated areas of the central nervous system. It is a poor glass former, making it unsuitable for vitrification in concentrations which can be introduced by perfusion at acceptable temperatures.

It is an on-going effort to search for CPAs with high penetrating ability, low toxicity, low viscosity, strong freezing point depression, and good glass forming characteristics. The present invention discloses a class of new glycol ether cryoprotective agents with excellent overall properties.

The rate and uniformity with which tissues are cooled after perfusion with CPA are crucial parameters for both organ cryopreservation and cryonics. Cooling rate affects the distribution and size of ice crystals formed during freezing. Intercellular ice crystals formed during rapid cooling are typically smaller and less injurious than those formed during slow cooling. CPA toxicity is also greatest at high temperatures. Rapid cooling minimizes CPA exposure time at high sub-zero temperatures, thereby reducing toxic effects.

Rapid cooling is essential for vitrification. With rapid cooling not only are the toxic effects of the CPA minimized, but the concentration of CPA needed to vitrify is also reduced. Vitrification with non-lethal CPA concentrations typically requires cooling rates of several degrees per minute. Cooling uniformity is also important because vitrified organs may fracture if exposed to temperature gradients near their glass transition temperature.

In the prior art the completion of CPA perfusion, cooling is typically performed by immersing organs or cryonics patients in cold fluids for external cooling. Achievable cooling rates range from $10°$ C. per minute for 8 ml samples (G. M. Fahy et al, Physical problems with the vitrification of large biological systems, Cryobiology 27, 492–510 (1990)) to less than $0.1°$ C. per minute for cryonics patients (Cryonics: Reaching for Tomorrow, B. Wowk, M. Darwin, Alcor Life Extension Foundation, 3rd Edition, 1991.). Referring to 8 ml samples, Fahy et al write that larger samples must "inevitably" be cooled slower than $10°$ C. per minute, and that this conclusion is "ominous" given the need for even higher CPA concentrations to vitrify at slower cooling rates, and the already borderline toxicity of CPA concentrations needed while cooling at $10°$ C. per minute. Efforts for achieving vitrification of large organs by cooling methods of the prior art thus appear to be at an impasse.

Rapid rewarming is also beneficial for recovery from cryopreservation, as frozen tissue tends to recrystallize (grow larger damaging ice crystals) if it is rewarmed slowly. CPA exposure time, and associated toxicity is also reduced if rewarming is rapid. The rewarming requirements for vitrification are especially stringent, with heating rates greater than $100°$ C. per minute typically required to avoid devitrification (ice formation) during rewarming. Specialized RF heating systems have been developed for this purpose.

It is clear from the above discussion that relatively high concentration CPAs are required for both freezing and vitrification in organ cryopreservation and cryonics, but high concentration CPAs are damaging to biological materials because of the inherent toxicity of the CPAs. Several general principles for reducing high concentration CPA damage are known which, for example, include exposure to the highest CPA concentrations at reduced temperature and time; the use of special combinations of CPAs and carrier solvents which cancel each other's toxicities; the use of nonpenetrating CPAs that can substitute for a portion of the penetrating agent otherwise needed (see U.S. Pat. No. 5,217,860). Among them, the most important and most effective is to increase cooling/rewarming rate, as discussed earlier, which reduces the exposure time to high concentration CPAs as well as significantly suppresses the formation of ice crystals.

Therefore, an objective of the present invention is to provide a method for internally and rapidly cooling/rewarming a biological material below the freezing point of water by circulating a cooled or warmed inert fluid through its vascular system, so that good cryopreservation can be achieved for organs or large organisms.

Another objective of the present invention is to provide a method for maintaining an organ at low temperature in situ to cryopreserve the organ without removal from a living animal.

Still another objective of the present invention is to provide a class of new glycol ether CPAs with special properties suitable for cryopreservation purposes.

SUMMARY OF THE INVENTION

The present invention relates to a method for controlling temperature of a biological material at sub-zero temperatures comprising the steps:

perfusing an inert fluid through the vascular system of organs, tissues, animals (including whole humans), controlling the temperature of the inert fluid which circulates through the vascular system, whereby the inert fluid functions as a heat exchange medium cooling or rewarming the organs, tissues, animals and whole humans internally and quickly.

The cooling/rewarming rates of the internal cooling/rewarming method of the present invention are more than ten times faster than those that can be achieved by conventional external cooling/rewarming methods of prior art. Such rapid cooling will allow significant decrease in the concentration of cryoprotectants needed to vitrify, thus, enhance the prospects for successful cryopreservation of organs with non-toxic CPA mixtures. These cooling rates also for the first time open the possibility of vitrifying whole humans.

In addition, the present invention can also be used to cool with extreme uniformity. By maintaining a small temperature difference between the organ and the fluid input, organs can be cooled or rewarmed in a uniform controlled manner without the temperature gradients that would otherwise accompany external cooling methods.

The present invention also provides a class of new glycol ether CPAs with special properties suitable for cryopreservation purposes.

While cooling of organs by perfusion with cold fluid for the purpose of freezing (A. A. Beisang et al, Damage assay of kidneys frozen by intraarterial perfusion with a fluorocarbon, Federation Proceedings, Vol. 29, No. 5, Sept.-Oct, 1970) and vitrification (D. Skrecky, Vitrification proposal, CryoNet Message #5174, Nov. 14, 1995.) has been suggested previously, the identification of suitable fluids and processes for cooling to below $-100°$ C. without injury is novel. The detailed problems and promise of cold fluid perfusion presented in this invention have not been documented previously.

DETAILED DESCRIPTION OF THE INVENTION

Generally, the method of the present invention comprises cooling a living biological material to be cryoprotected to a temperature between about 0–15° C., perfusing the biological material with a CPA solution, and subsequently perfusing with an inert fluid to replace the CPA solution until the vascular system is cleared of the CPA, then cooling the inert fluid to a desired low temperature and circulating it through the vascular system of the biological material until a desired temperature is achieved for the biological material. The inert fluid functions as an internal heat exchange medium which significantly promotes the cooling/rewarming process by allowing direct heat exchange between the fluid and the wall of the vascular system. Compared with the external cooling method of the prior art, the surface area for heat exchange is increased tremendously with the internal cooling method of the present invention and, thus, heat exchange rate is enhanced significantly by increased heat conduction. The cooled inert fluid is circulated continuously through the vascular system which promotes heat exchange by enhanced heat convection. Therefore, the overall cooling rate is increased significantly. By replacing vascular water that might otherwise freeze, the inert fluid also provides a cryoprotective effect.

The lowest temperature which can be achieved by the internal cooling method of the present invention is determined by the pour point of the inert fluid, which can be as low as $-180°$ C. The inert fluid can be cooled by passage through a heat exchanger that is cooled by refrigeration, by thermal contact with a large cold heat sink, by circulation of a cold fluid, or by cold gas. In the present implementation of the invention, cold nitrogen gas generated from boiling liquid nitrogen is fan-driven past a heat exchange unit to cool the inert fluid.

The Inert Fluid

The inert fluid of the present invention can be any chemical or mixtures thereof that remain liquid at low temperatures with low viscosity and low toxicity. Preferred inert fluids of the present invention include fluorocarbons, polysiloxanes (silicones), fluorosilicones. They can be used in pure form or as mixtures. Agents of these classes are typically innocuous to living systems.

Fluorocarbons, particularly perfluorocarbons, have begun to see wide application in medicine (J. G. Riess, Overview of progress in the fluorocarbon approach to in vivo oxygen delivery, Biomater-Artif-Cells-lmmobilization-Biotechnol., 20(2–4): 183–202 (1992)) as blood substitutes (emulsions), intra-ocular tamponades, and liquid ventilation media (as pure agents). Perfluorocarbons are generally insoluble in both lipids and water, and thus ideally suited as inert non-toxic perfusates in biological systems. Vascular perfusion with pure FC-72 (perfluorohexane) accompanied with fixation preserves endothelial ultrastructure extremely well (D. E. Sims, M. M. Horne, Non-aqueous fixative preserves macromolecules on the endothelial cell surface: an in situ study, Eur-J-Morphol. Mar; 32(1): 59–64 (1994)), consistent with the expectation that pure perfluorocarbon is non-toxic intravascularly. Rat hearts have been perfused with pure fluorocarbon and demonstrated subsequent recovery (F. Gollan, L. C. Clark, Organ perfusion with fluorocarbon fluid. Physiologist 9:191, 1966).

Example perfluorocarbons for this invention include FC-72 (pour point −90° C., viscosity 1.9 centistokes at −79° C.), FC-87 (pour point −101° C., viscosity 2 centistokes at −90° C.), PF-5050 (pour point −115° C., viscosity 5 centistokes at 100° C. ), FC-77 (pour point −95° C.) and mixtures thereof. FC-77 and FC-87 are isomers homologues of perfluoroalkanes, and are products of Minnesota Mining and Manufacturing (3M) Co. Following initial cooling by these or similar agents, it's then also possible to transition to perfluorobutane isomeric mixtures (PF-5040, pour point −128° C., boiling point −2° C.), or perfluoropropane mixture (PF-5030, pour point −183° C., boiling point −37° C.) to continue cooling into the deep sub-zero range.

Many perfluorocarbon mixtures freeze (crystallize) at temperatures not far below their pour point. Such mixtures are not preferred for this invention. Mixtures containing FC-77 are a notable exception. FC-77 is found to vitrify rather than freeze during deep cooling. FC-77 behaves as a fluorocarbon cryoprotectant, depressing the pour point, and enhancing glass formation in other perfluorocarbons to which it is added. For example a mixture of 20% FC-77 and 80% FC-87 remains liquid from +30° C. down to −140° C., which is an ideal temperature span invention. This mixture vitrifies at temperatures below −140° C., avoiding any damage that would be caused by fluorocarbon ice crystals. Clearly other perfluorocarbon mixtures affording similar mutual cryoprotective properties are possible in the spirit of this invention.

Other fluorocarbons, such as fluoroethers, hydrofluoroethers, or hydrofluorocarbons may also be used for the invention, although they are less preferred due to decreased inertness.

Siloxanes, particularly low molecular weight dimethyl siloxane polymers (silicones), are non-reactive, non-toxic fluids that retain low viscosity well into the sub-zero range. Octamethyltrisiloxane, for example, remains fluid down to −80° C. The associated monomer, tetramethylsilane (although less inert) remains a liquid to −99° C. Proprietary siloxane mixtures with even lower pour points are available from Dow Chemical company. Siloxanes are suitable for inert fluid cooling when the target temperature is relatively high, and a fluid of low physical density is desired. For lower temperatures, fluorocarbons are preferred.

Fluorosilicones (such as polymethyl-3,3,3-trifluoropropylsiloxane) are a class of compounds intermediate in density between silicones and fluorocarbons, and may be used at relatively high temperatures when a fluid of density near that of water is preferred.

Cryoprotective Agent

The present invention also discloses the use of new CPA solutions containing glycol ethers in a cryopreservation process. For this invention, "glycol ethers" are understood to comprise chemical compounds containing alkoxy, and particularly methoxy functional groups. Exemplary classes include alkoxylated alkanes, alkoxylated alcohols and polyols, as well as other alkoxylated organics.
Alkoxylated alkanes, include:
  methoxylated ethanes, such as 1,2-dimethoxyethane; and
  methoxylated propanes, such as 1,2,3-trimethoxypropane.
Alkoxylated alcohols and polvols, include:
  methoxylated ethanols, such as 2-methoxyethanol;
  methoxylated propanols, such as 1-methoxy-2-propanol or 1,3-dimethoxy-2-propanol;
  methoxylated butanols, such as 1-methoxy-3-butanol;
  methoxylated propanediols, such as 2-methoxy-1,3-propanediol or 3-methoxy-1,2-propanediol; and
  methoxylated butanediols, such as 1,4-dimethoxy-2,3-butanediol.

Other alkoxylated organics, include:
  methoxylated ethers, such as (poly)glyme solvents;
  methoxylated ketones, such as methoxyacetone or 1,3-dimethoxy-2-propanone;
  methoxylated amines; and
  methoxylated sulfones.

The particular compounds shown above are examples only, and clearly do not exhaust the possibilities for each class. It will be understood by those skilled in the art that various modifications to the these example classes are possible, such as methylation to increase glass forming properties. Thus, there are a number of additional compounds which can be effectively used within the spirit and scope of this invention. Any compounds which are produced as a result of alkoxylation to improve cryoprotective properties are contemplated.

CPAs protect biological systems during cooling by interacting with water (hydrogen bonding) in a manner that prevents the ordering of water molecules (freezing) at low temperatures. Interaction with water is usually achieved by including hydroxyl (OH), amine (NH2), or other polar groups as part of the CPA molecule. The disadvantage of polar groups with highly localized positive and negative charge is that such groups not only bond with water, but also hydrogen bond with similar groups on adjacent CPA molecules. This strong interaction between CPA molecules is undesirable because it increases solution viscosity (making perfusion and tissue permeation difficult), and decreases ice-inhibition and glass forming ability.

As an alternative to the hydroxylation of the prior art, methoxylation (inclusion of O—CH3 groups) offers the advantage of decreased interaction between CPA molecules while still preserving strong water interaction. The decreased interaction between CPA molecules is achieved by more widely distributing the positive charge that would otherwise be highly localized on a single hydrogen in a hydroxyl group. Without a localized positive charge on the CPA molecule, oxygen atoms in adjacent CPA molecules no longer have a bonding target. However the localized negative charge on the oxygen atoms remain, providing a bonding target for the hydrogen in water molecules. This reduction in CPA—CPA interaction maximizes the availability of bonding sites for water, which increases ice inhibition and glass forming properties. Viscosity is also greatly reduced, and permeation kinetics are improved.

As expected, glycol ethers are a highly penetrating class of compounds that typically pass through cell membranes faster than other molecules of similar size, including amides and alkylamides (the most penetrating class of CPAs previously known). This rapid penetration allows rapid equilibration between intracellular and extracellular CPA concentration, minimizing tissue dehydration and osmotic injury. It also minimizes time necessary for equilibration, so that tissues need not be exposed to high CPA concentrations at high temperatures for great lengths of time, thereby minimizing toxic effects.

Glycol ethers possess very low viscosity compared to conventional CPAs, and exhibit good (non-colligative) freezing point depression. This makes them ideally suited for introduction and removal from tissue at sub-zero temperatures, where toxicity can be minimized.

Glycol ethers generally, and 2-methoxyethanol in particular, strongly inhibit ice formation during both cooling and rewarming. This is consistent with the present commercial use of 2-methoxyethanol as a jet fuel de-icing additive.

Glycol ethers are good to excellent glass formers. In Tables I-A through I-D, experimental data for conventional cryoprotectants and the CPAs according to the present invention are provided. Glycol ethers achieve high penetration while in many cases still retaining a modest lipidiwater partition coefficient (a measure of hydrophobicity, which correlates with toxicity). Table I-E shows toxicity data for several CPA mixtures containing glycol ethers.

TABLE I-A

Conventional Cryoprotectants

| AGENT | STRUCTURE | CNV | STAB-ILITY | VISC. | PERM-EANCE |
|---|---|---|---|---|---|
| Ethylene Glycol | $HOCH_2CH_2OH$ | 54% | stable | 25 | 3.4 |
| Propylene Glycol | $CH_3(CHOH)CH_2OH$ | 47% | unstable | 60 | 1.8 |
| Glycerol | $HOCH_2(CHOH)CH_2OH$ | 59% | unstable | 1400 | 0.6 |

TABLE I-B

Methoxylated Analogs of Cryoprotectants

| AGENT | STRUCTURE | CNV | STAB-ILITY | VISC. | PERM-EANCE |
|---|---|---|---|---|---|
| 2-Methoxy ethanol | $HOCH_2CH_2OCH_3$ | 49% | stable | 1.7 | 12 |
| 1-Methoxy-2-propanol | $CH_3(CHOH)CH_2OCH_3$ | 45% | semi-stable | 2.0 | 7 |
| 3-Methoxy-propanediol | $HOCH_2(CHOH)CH_2OCH_3$ | 54% | semi-stable | 80 | 1.0 |

TABLE I-C

Other Examples of Glycol Ethers of the Present Invention

| AGENT | STRUCTURE | CNV | STAB-ILITY | VISC. | PERM-EANCE |
|---|---|---|---|---|---|
| Dimethoxy ethane | $CH_3OCH_2CH_2OCH_3$ | 42% | stable | 0.5 | 20 |
| Diglyme | $CH_3O(CH_2CH_2O)_2CH_3$ | 50% | stable | 1 | 10 |
| Tetraglyme | $CH_3O(CH_2CH_2O)_4CH_3$ | 51% | stable | 5 | 6.8 |

TABLE I-D

Exemplary Mixture

| AGENT | CNV | STA-BILITY | VISC. | PER-MEANCE |
|---|---|---|---|---|
| 2:1 (v/v) Glycerol:Methoxyethanol | 56% | semi-stable | 60 | 4.4 (mean) |

CNV: Minimum concentration (w/w) needed to vitrify in pure water during cooling at a rate of 10° C. per minute.
Stability: Stability (resistance to ice formation) of vitreous solution at CNV during rewarming at a rate of 10° C. per minute from −60° C..
Visc: Viscosity (centipoise) of pure agent at 20° C..
Permeance: Relative rate of penetration across human red blood cell membrane.

TABLE I-E

Toxicity of Glycol Ether Mixtures

| MIXTURE | VIABILITY |
|---|---|
| Control | 100% |
| VS4/2-Methoxyethanol | 98% |
| VS4/2-Ethoxyethanol | 95% |
| VS4/Triglyme | 93% |

TABLE I-E-continued

Toxicity of Glycol Ether Mixtures

| MIXTURE | VIABILITY |
|---|---|
| VS4/1,3-Dimethoxy-2-propanol | 93% |
| VS4/1-Methoxy-2-propanol | 89% |
| VS4/1,2-Dimethoxyethane | 85% |

VS4/Glycol Ether refers to a VS4 mixture (as per patent #5,217,860) in which propylene glycol is substituted by the Glycol Ether. Viability is measured in a kidney slice model as in the above patent after exposure to a peak CPA concentration of 40% for 10 minutes at 0° C.

Large animals can be perfused with high concentrations of glycol ethers near 0 C with rapid equilibration, no dehydration, no edema or other visible evidence of toxic effects. Histologic preservation is excellent at microscopic and ultrastructural levels.

The inclusion of glycol ethers in perfusion solutions is a new and promising approach to the reduction of cryoinjury in organs, tissues and humans cooled to sub-zero temperatures. In preferred embodiments of the present invention, 2-methoxyethanol and 1-methoxy-2-propanol have been used in perfusion solutions. Two glycol ethers (2-methoxyethanol and 1,3-dimethoxy-2propanol) have occasionally been used for cryopreservation of embyos and cell suspensions (Refs. 20–23). However, to our knowledge, the special properties and utility (particularly glass forming ability) of these compounds, or methoxylated compounds generally, for cryoprotection of vascular tissue have not been documented until now.

CPA Perfusion

According to the present invention, the step to introduce a CPA solution into an organ can be carried out in different ways, but usually through vascular perfusion. The perfusion of an organ or any other biological materials usually starts with a dilute CPA solution. Concentration of the CPA solution is gradually increased to a predetermined level while the perfusion proceeds. Concentrations of the CPA both at the inlet and the outlet of the vascular system are monitored by concentration sensors, which help determine the completion of the CPA perfusion (achieved when inflow and outflow concentrations are nominally identical). Any CPAs or mixtures thereof known to the art can be used in the present invention. But it is preferred to include the glycol ethers mentioned earlier, more preferred to use or include 2-methoxyethanol or 1-methoxy-2-propanol. CPA perfusion is usually conducted at a temperature between about −30 to 15° C. depending on several factors such as temperature dependence of toxicity and viscosities of particular CPAs, the size of organs, and the desired perfusion rate. For example, lower temperature usually reduces the toxic effects of CPA, but also reduces flow rate of the cryoprotectant which may not be desirable. The rate of CPA perfusion is limited by several factors including permeability of the agent into the cell and the size of the organ to be perfused. The time required to complete a CPA perfusion varies from few minute to few hours. For example, in one 30 preferred embodiment of the present invention, the perfusion of a 20 kg dog takes 45 minutes to complete with 2-methoxyethanol, 2.3 hours with 3methoxy-1,2-propanediol. It is not necessary to conduct the perfusion isothermally, i.e. during perfusion the temperature can be reduced gradually which gives the benefit of high perfusion rate at low CPA contractions and low temperature at high CPA concentration.

Replacing CPA with Inert Fluid

According to the present invention, in a typical cooling application, an organ is perfused with isothermic inert fluid at the completion of CPA perfusion. Perfusion with the inert fluid is continued until the vascular system is substantially cleared of the CPA solution. As there is no need to let the inert fluid permeate into cells, perfusion with the inert fluid can be conducted as fast as possible. The perfusion rate of the inert fluid is usually in the range of the basal blood flow rate, depending on the biological material to be cryoprotected and the viscosity of the inert fluid used. This perfusion is conducted at temperatures similar to those used for CPA perfusion. It is very important to wash out the CPA perfusate completely from the vascular system, otherwise the remaining CPA perfusate will block the flow path of the vascular system when the inert fluid is cooled to very low temperatures.

Effective replacement of aqueous CPA perfusate with inert fluid is difficult due to the differing physical properties of the two liquids. The inert fluid is usually immiscible with CPA solution and water, typically 50%–100% more dense than water, and viscosities of those fluids suitable for deep cooling are typically lower than water. Two serious problems are caused by these differences in physical properties: (1) Density differences and immiscibility lead to the formation of water "bubbles" in some parts of the vasculature. These aqueous "bubbles" will freeze (or vitrify) during deep cooling and plug pathways in the vasculature causing failure of inert fluid perfusion. (2) The low viscosity inert fluid tends to shunt flow, preferentially following the first clear arterio-venous pathways, leaving downstream vasculature filled with higher viscosity aqueous perfusate. These downstream areas of failed inert fluid perfusion will not experience proper heat transfer during inert fluid cooling/rewarming.

Several techniques are developed according to the present invention to minimize these problems. The shunt flow problem is most easily addressed by employing a series of inert fluids with different viscosities, i.e. initially perfusing with a high viscosity inert fluid comparable to that of the aqueous CPA perfusate to wash out the aqueous perfusate, followed by progressive dilution of the high viscosity fluid with a miscible low viscosity fluid suitable for deep cooling.

Although the high viscosity inert fluid used for the initial perfusion is preferably miscible with the inert fluid for later deep cooling, an immiscible initial fluid can be used as long as it does not freeze at deep cooling temperatures. Furthermore, as different compounds have different temperature dependence of viscosity, a proper perfusion temperature sometimes is available to help mach the viscosities. Thus, use of a series of inert fluids with different viscosities can be used to aid introduction and removal of inert fluids from the vascular system.

The problem of immiscibility (aqueous bubble formation) can be solved by the inclusion of water/inert fluid surface active agents (surfactants) to emulsify the water/inert fluid phases. Typical water/inert fluid surfactants used in the present invention include polyoxypropylene/polyoxyethylene copolymers, although other surfactants (particularly ionic fluorocarbon surfactants) can also be used. Concentrations of surfactants are usually in a range of several percent. The inert fluid can also be introduced and removed as an aqueous emulsion of progressively increasing and decreasing density respectively. In such aqueous emulsions, the inert fluid content preferably varies from 0–100% w/w, more preferably 30–95%, still more preferably 50–90%. The CPA solution content preferably varies from 100–0% w/w, more preferably from 70–5%, still more preferably from 50–10%. The surfactant content is preferably in a range of 0–10% w/w, more preferably from 1–5%. In one preferred embodiment of the present invention, the inert fluid is introduced initially as an emulsion mixture of FC-87, 46% w/w aqueous solution of 1-methoxy-2-propanol and Pluronic F-68 surfactant in which FC-87 counts 60% w/w, the 46% w/w aqueous solution of 1-methoxy-2-propan counts 39% w/w, and the rest is the surfactant. (The transition to pure inert fluid being made following perfusion with maximum-density emulsion.) Alternatively, the densities of the aqueous and inert fluid phases can be altered by mixing with compatible solutes or colloids at the time of fluid introduction and removal.

Circulating Cooled Inert Fluid through Vascular System

Following complete replacement of aqueous perfusate by inert fluid of composition suitable for deep cooling, the input temperature of the fluid is then reduced until a desired temperature difference with respect to the organ is achieved. In one preferred embodiment of the present invention, The initial temperature difference between the inert fluid and the organ is preferably set to be within the range from approximately 20° C. to approximately 200° C. more preferably this difference is within the range from approximately 50° C. to approximately 150° C. In a particularly preferred embodiment, the temperature difference is 100° C. Perfusion of the inert fluid continues until the organ reaches the desired target temperature. The inert fluid can be a pure compound or a mixture. During deep cooling, the composition of the inert fluid can be changed easily. There are many ways to manipulate the combinations of different inert fluids. For example, the deep cooling can be started with an inert fluid with a relatively high pour point such as FC-72 and replaced later with an inert fluid with a relatively low pour point such as PF-5030. It is impossible to exhaust all possible combinations of different inert fluid and CPAs according to the present invention, but it is obvious according to the present invention that different combinations can be used for different purposes, which is within the spirit and scope of the present invention.

Cooling Rate of the Present Invention

The rate at which an organ can be cooled depends upon the temperature difference between the organ and fluid (at input), the mass of the organ, the fluid flow rate, and the heat capacity of the inert fluid. Basal blood flow rates in various organs and the whole body of a 55 kg adult are given by Guyton (Textbook of Medical Physiology, A. C. Guyton, W. B. Saunders Company, 1986.) as in the following Table II:

TABLE II

| ORGAN | LITERS/MIN. | LITERS/MIN./KG |
|---|---|---|
| Kidney | 0.55 | 3.6 |
| Liver | 1.35 | 0.95 |
| Brain | 0.7 | 0.5 |
| Body | 5.0 | 0.09 |

Clearly a high flow rate of the inert fluid is desirable. Because viscosities of some of the inert fluids of the present invention are less than that of blood, a flow rate of the inert fluid as high as several times basal blood flow rate can be easily achieved. If necessary, the perfusion pressure can be increased beyond normal physiologic values to further enhance the flow rate of the inert fluid. In addition, once the organ is cooled to a sufficiently low temperature that it is nearly solid, a pump can he used at the outlet of the vascular system to generate a low pressure on the outlet side so as to further promote the inert fluid circulation.

The heat capacity of perfluorocarbons is typically half that of water per unit volume. The passage of perfluorocarbon volume equal to an organ's own volume would thus be expected to lower the organ temperature approximately halfway toward the fluid input temperature. Assume the initial temperature of tissue is 0° C. Perfusion with fluid is begun with an input temperature of −100° C., and flow rate equal to twice the basal blood flow rate. Expected initial and final cooling rates are shown in Table III. (A temperature of −90° C. is taken to be the final target because below this temperature CPA toxicity and risk of freezing during vitrification are greatly reduced, and cooling can proceed more leisurely.)

TABLE III

| ORGAN | INITIAL COOLING RATE (AT 0° C.) | FINAL COOLING RATE (AT −90° C.) |
|---|---|---|
| Kidney | 360° C./min. | 36° C./min. |
| Liver | 95° C./min. | 10° C./min. |
| Brain | 50° C./min. | 5° C./min. |
| Body | 9° C./min. | 1° C./min. |

The cooling rates shown in Table III are more than ten times greater than can be achieved by previous external cooling methods. Such rapid cooling will allow significant decreases in the concentration of cryoprotectants needed to vitrify, enhancing the prospects for successful cryopreservation of organs with non-toxic CPA mixtures. These cooling rates also for the first time open the possibility of vitrifying whole humans.

Rewarming

Finally, the invention can also be used for rapid rewarming of organs previously cooled by inert fluid perfusion. In this application, the organ would first be rewarmed by external means to a temperature at which the previously perfused fluid becomes liquid (−100° C. for FC-87). The organ would then be perfused with warm inert fluid at a temperature within the range from about 30 to about 15° C., more preferably from about −5 to about 5° C. In one particularly preferred embodiment of the present invention, the rewarming process is conduced with a warm inert fluid at about 0° C. A rewarming process would give initial and final rewarming rates comparable to the cooling rates in Table III (except that the initial and final temperatures would be reversed). With rewarming rates in excess of 300° C./minute achievable for well-vascularized organs such as the kidney, the invention is a possible alternative technology to RF heating for rewarming vitrified organs, or for rewarming frozen organs without recrystallization injury. All the techniques used for deep cooling according to the present invention are applicable to the rewarming.

For the rewarming application, it is crucial that dissolved gases that typically accumulate in cold inert fluids be removed during rewarming to prevent gas embolism. This can be achieved by transiently lowering the pressure on the warm side of the perfusion circuit (such as by stirring, venturi flow, or a vertical excursion of the perfusion circuit) causing dissolved gases to come out of solution and be captured in a bubble trap. Transient overheating (followed by re-cooling) in part of the circuit is also effective.

EXAMPLES

In this example, two 20 kg leaving adult dogs are tested for cooling and rewarming the whole body. One of the dogs is cooled and rewarmed using the internal cooling/rewarming method of the present invention. The other is cooled and rewarmed using the conventional external cooling/rewarming method as control test. The experiment is conducted as follows:

First the dogs are anaesthetized and subjected to surface cooling with ice bags. The next step is to access the animal's vasculature via the femoral vessels. Then the whole body is cooled to about 15° C. The blood is washed out using MSHP2 base perfusate, and the body is further cooled to 5° C., then perfused with 2-methoxyethanol at 5° C. The introduction of the cryoprotectant 2-methoxyethanol is conducted with two containers: At the beginning the first container contains base perfusate with no 2-methoxyethanol, the second container contains a 35% w/w 2-methoxyethanol solution in base perfusate. The first container is connected to the inlet of the vascular system of the dog and pumped into the vascular system, while the second container continuously provides the first container with the 35% 2-methoxyethanol CPA solution, so that concentration of 2-methoxyethanol in the first container increases gradually and reaches to the level of 35% of 2-methoxyethanol. The perfusion of 2-methoxyethanol last about 45 minutes.

After the completion of 2-methoxyethanol solution perfusion, the 2-methoxyethanol solution within the vascular system of one of the two dogs is replaced with FC-72 by circulating the FC-72 through the vascular system at about 5° C. The flow rate of the FC-72 is about 7 liter/min. The replacement process lasts about ten minutes, and the 2-methoxyethanol is completely removed. Then the two dogs are put into a alcohol-dry ice bath separately, ready for deep cooling.

For the deep cooling, the initial bath temperature is about −35° C. One dog is allowed to cool solely by contact with the alcohol bath (the external cooling method of the prior art). The other dog is cooled by circulating the inert fluid FC-72 at a flow rate of about 6 liter/min, at a starting temperature of −10° C. , and subsequent adjustment of the fluid temperature to remain 2° C. below the measured esophageal temperature. This temperature differential resulted in a cooling rate of about 0.25° C. per minute, a relatively slow rate which was chosen to avoid intracellular freezing (the animal not having been perfused with a vitrifiable concentration of 2-methoxyethanol).

The cooling rates for the inert fluid cooled dog and externally cooled dog are substantially different. It takes about 210 minutes for rectal temperature to drop to −17° C., for esophageal temperature to drop to −10° C. in the case of the external cooling. While in the case of the internal cooling of the present invention, temperatures decrease sharply at the beginning of the cooling process, −10° C. is almost immediately reached, and at 210 minute rectal temperature already drops to about −47° C and esophageal temperature to about −45° C. The cooling rate of the method of the present invention is significantly higher than that of the external cooling method of the prior art, especially, at beginning stage. The initial quick drop of the temperature to certain low value helps to minimize the toxic effects of the CPA solution and, therefore, is very desirable.

The cooled dogs are also tested with rewarming from −90 to about −5° C. Bath temperature is set at about −5° C. initially in the rewarming process. The initial temperature of the dogs is about −80° C. During the rewarming process, for one dog, FC-72 at a inlet temperature of about 0° C. is circulated through the vascular system, while the other dog is warmed only by placement in the bath. The rewarming rate of the present invention is much faster than that of the external rewarming method of the prior art. After the first 15 minutes, temperatures of right tympanic, esophageal and rectal probes have reached −14° C., −26° C. and −42° C. respectively in the case while in the case of the external rewarming method, the corresponding temperatures are about −28° C., −73° C. and −60° C. To reach similar temperatures as the present invention, it takes several hours more for the external rewarming method. The rewarming rates achieved in this example are representative of the cooling rates that can also be achieved if the inert fluid/tissue temperature differential is maximized on cooling (as would be done if vitrification was the objective).

Other Aspects of the Invention

In addition to extremely rapid cooling, the invention can also be used to cool with extreme uniformity. By providing a large heat exchange surface area and maintaining a small temperature difference between the organ and the fluid input, organs can be cooled or rewarmed in a uniform controlled manner without the temperature gradients that would otherwise accompany external cooling methods.

In still other applications, the invention can be used to maintain an organ at low temperature in situ without removal from a living animal. For example, protocols for central nervous system cryopreservation might be studied by selectively perfusing and cooling the brain to low subzero temperature while maintaining the rest of the animal at a higher temperature compatible with later recovery.

Conclusion

The method of the present invention allows cooling and subsequent rewarming from temperatures lower than −100° C. at rates exceeding 100° C. per minute for some organs. These rates are much higher than can be achieved by external heat transfer methods, and will allow significant reduction of the concentration of cryoprotective agents needed to achieve reversible vitrification of organs for long-term banking. Heat transfer by inert fluid perfusion is also beneficial for reducing ice crystal damage and cryoprotectant toxicity during ordinary freezing and thawing.

The present invention also provides a class of new cryoprotective agent (glycol ethers) for reduction and prevention of ice formation during cooling of vascular tissues and organs. Glycol ethers generally, and methoxylated compounds in particular, are highly penetrating agents that equilibrate rapidly upon perfusion, and exhibit strong ice inhibition and glass forming properties. The low viscosity and freezing point of these compounds also make them well suited for sub-zero perfusion to minimize toxic effects. Toxicities are compatible with the potential use of glycol ethers in perfusate solutions for reversible cryopreservation of organs and large organisms by freezing or vitrification.

REFERENCES (1) U.S. Pat. No. 4,559,298 G. M. Fahy, Cryopreservation of biological materials in a non-frozen vitreous state, Dec. 1985.

(2) U.S. Pat. No. 5,217,860 G. M. Fahy, Method for preserving organs for transplant by vitrification, Jun. 1993.

(3) Organ Preservation for Transplantation, Editors: A. M. Karow, D. E. Pegg, Marcel Dekker, Inc., 2nd Edition, 1981.

(4) The Prospect of Immortality, R. C. W. Ettinger, Doubleday, 1964.

(5) Cryonics: Reaching for Tomorrow, B. Wowk, M. Darwin, Alcor Life Extension Foundation, 3rd Edition, 1991.

(6) G. M. Fahy et al, Vitrification as an approach to cryopreservation, Cryobiology 21, 407–426 (1984).

(7) G. M. Fahy et al, Some emerging principles underlying the physical properties, biological actions, and utility of vitrification solutions, Cryobiology 24, 196–213 (1987).

(8) G. M. Fahy et al, Physical problems with the vitrification of large biological systems, Cryobiology 27, 492–510 (1990).

(9) P. S. Ruggera, G. M. Fahy, Rapid and uniform electromagnetic heating of acqueous cryoprotectant solutions from cryogenic temperatures, Cryobiology 27, 465–478 (1990).

(10) J. R. Sparrow et al, Fibroblast behavior at aqueous interfaces with perfluorocarbon, silicone, and fluorosilicone liquids, Invest-Ophthalmol-Vis-Sci. Apr; 31(4): 638–46 (1990).

(11) McGraw Hill Encyclopedia of Science & Technology, Volume 16, p. 437, 1992.

(12) M. Darwin, H. Hixon, Evaluation of heat exchange media for use in human cryonic suspensions, Cryonics, July, 1984.

(13) J. G. Riess, Overview of progress in the fluorocarbon approach to in vivo oxygen delivery, Biomater-Artif-Cells-lmmobilization-Biotechnol., 20(2–4): 183–202 (1992).

(14) D. E. Sims, M. M. Horne, Non-aqueous fixative preserves macromolecules on the endothelial cell surface: an in situ study, Eur-J-Morphol. Mar; 32(1): 59–64(1994).

(15) Textbook of Medical Physiology, A. C. Guyton, W. B. Saunders Company, 1986.

(16) B. Wowk, In-situ brain cooling, CryoNet Message #6611, Jul. 25, 1996.

(17) D. Skrecky, Vitrification proposal, CryoNet Message #5174, Nov. 14, 1995.

(18) F. Gollan, L. C. Clark, Organ perfusion with fluorocarbon fluid. Physiologist 9:191, 1966.

(19) A. A. Beisang, J. Feemster, R. H. Dietzman, H. Uchida, J. E. Carter, E. F. Graham, R. C. Lillehei, Damage assay of kidneys frozen by intraarterial perfusion with a fluorocarbon, Federation Proceedings, Vol. 29, No. 5, September-October, 1782.1788, 1970.

(20) K. A. Santarius, J. Bauer, Cryopreservation of spinach chloroplast membranes by low-molecular-weight carbohydrates, Cryobiology 20, 83–89 (1983).

(21) Takagi et al, Survival rate of frozen-thawed bovine IVF embryos in relation to exposure time using various cryoprotectants, Cryobiology 30, 306–312 (1993).

(22) Takagi et al, Postthaw viability of the inner cell mass of in vitro-matured/in vitro-fertilized embryos frozen in various cryoprotectants, Cryobiology 31, 398–405 (1994).

(23) Schuff-Werner P, Muller U, Unger C, Nagel GA, Eibl H, 1-O-methyl-rac-glycerol: a new agent for the cryopreservation of mononuclear cells, Cryobiology 25, 487–494 (1988).

What is claimed is:

1. A method for controlling temperature of a biological material having a vascular system at sub-zero degree Centigrade temperatures, comprising the following steps:

perfusing the biological material with an inert fluid through the vascular system of the biological material;

controlling temperature of the inert fluid before entering the vascular system; and circulating the temperature-controlled inert fluid through the vascular system, whereby the inert fluid functions as a heat exchange medium for cooling or warming the biological material internally, wherein the inert fluid comprises a polysiloxane or a fluorosilicone.

2. The method of claim 1, wherein the inert fluid further comprises a fluorocarbon.

3. The method of claim 1, wherein the inert fluid further comprises a polysiloxane.

4. The method of claim 1, wherein the inert fluid further comprises a fluorosilicone.

5. The method of claim 1, wherein the inert fluid further comprises a perfluorocarbon mixture comprising FC-77.

6. The method of claim 1, wherein the inert fluid further comprises a mixture of 10% to 50% FC-77, with the remainder being FC-87.

7. The method of claim 1, wherein the inert fluid comprises a mixture or emulsion of said polysiloxane or fluorosilicone with at least one fluid selected from the group consisting off fluorocarbons, fluorosilicones and polysiloxanes.

8. The method of claim 1, wherein an aqueous perfusate is in the vascular system of the biological material prior to the inert fluid perfusing step.

9. The method of claim 8, wherein a surface active agent is added to the inert fluid and/or to the aqueous perfusate.

10. The method of claim 8, wherein the inert fluid and/or the aqueous perfusate further comprises colloids or other solutes.

11. The method of claim 8, wherein a gas that is soluble in both water and inert fluid is perfused into the vasculature to displace aqueous perfusate prior to inert fluid perfusion and/or to displace inert fluid prior to reperfusion with aqueous perfusate.

12. The method of claim 11, wherein the gas is carbon dioxide.

13. The method of claim 1, further comprising, prior to the inert fluid perfusing step, perfusing said biological material with a solution comprising a cryoprotective agent (CPA).

14. The method of claim 1, wherein said vascular system has an inlet in which the inert fluid is introduced, and wherein the inert fluid has a initial temperature at the inlet of the vascular system which is approximately 50° C. to approximately 150° C. less than the temperature of the vascular system to achieve cooling of the biological material.

15. The method of claim 1, wherein the biological material is at a temperature lower than the inert fluid, and wherein the inert fluid has an initial temperature at the inlet of the vascular system within the range from about −30° C. to about 15° C. to achieve warming of the biological material.

16. The method of claims 15, further comprising a step of removing dissolved gases from the inert fluid during warming.

17. The method of claim 1, wherein the inert fluid is perfused in the perfusing step at a flow rate equal to about 1–6 times of basal blood flow rate through said biological material.

18. The method of claim 1, wherein the biological material is selected from the group consisting of organs, tissues, and whole animals.

19. The method of claim 1, wherein the inert fluid functions to cool the biological material to vitrify said biological material.

20. A method for controlling temperature of a biological material having a vascular system at sub-zero degree centigrade temperatures, comprising:

perfusing the biological material with an inert fluid through the vascular system of the biological material;

controlling temperature of the inert fluid before entering the vascular system; and circulating the temperature-controlled inert fluid through the vascular system, whereby the inert fluid functions as a heat exchange medium for cooling or warming the biological material internally, wherein an aqueous perfusate is in the vascular system of the biological material prior to the perfusion of the inert fluid, and wherein a gas that is soluble in both water and the inert fluid is perfused into the vasculature to displace said aqueous perfusate prior to inert fluid perfusion and/or to displace the inert fluid prior to reperfusion with aqueous perfusate.

21. The method of claim 20, wherein the gas is carbon dioxide.

* * * * *